(12) United States Patent
Jorgenson et al.

(10) Patent No.: US 11,439,568 B2
(45) Date of Patent: Sep. 13, 2022

(54) SMART PROMPTING TO IMPROVE RESPONDERS CPR PERFORMANCE

(71) Applicant: KONINKLIJKE PHILIPS N.V., Eindhoven (NL)

(72) Inventors: Dawn Blilie Jorgenson, Mercer Island, WA (US); Chenguang Liu, Bothell, WA (US)

(73) Assignee: Koninklijke Philips N.V., Eindhoven (NL)

(*) Notice: Subject to any disclaimer, the term of this patent is extended or adjusted under 35 U.S.C. 154(b) by 194 days.

(21) Appl. No.: 16/645,842

(22) PCT Filed: Sep. 18, 2018

(86) PCT No.: PCT/EP2018/075118
§ 371 (c)(1),
(2) Date: Mar. 10, 2020

(87) PCT Pub. No.: WO2019/057677
PCT Pub. Date: Mar. 28, 2019

(65) Prior Publication Data
US 2020/0297577 A1 Sep. 24, 2020

Related U.S. Application Data

(60) Provisional application No. 62/560,229, filed on Sep. 19, 2017.

(51) Int. Cl.
*A61H 31/00* (2006.01)
*A61N 1/39* (2006.01)
*A61B 5/08* (2006.01)

(52) U.S. Cl.
CPC .......... *A61H 31/005* (2013.01); *A61H 31/007* (2013.01); *A61N 1/3925* (2013.01); *A61N 1/39044* (2017.08); *A61N 1/3993* (2013.01); *A61B 5/0809* (2013.01)

(58) Field of Classification Search
CPC . A61H 31/005; A61H 31/007; A61N 1/39044
USPC .......................................................... 607/3
See application file for complete search history.

(56) References Cited

U.S. PATENT DOCUMENTS

| | | | |
|---|---|---|---|
| 8,942,803 B1 | 1/2015 | Herken et al. | |
| 2007/0060785 A1* | 3/2007 | Freeman | A61B 5/318 600/16 |
| 2008/0145827 A1 | 6/2008 | Strand et al. | |

(Continued)

FOREIGN PATENT DOCUMENTS

| | | |
|---|---|---|
| EP | 1491175 A1 | 12/2004 |
| WO | 2006136975 A2 | 12/2006 |

(Continued)

OTHER PUBLICATIONS

PCT/EP2018/075118, WO & ISR, Nov. 12, 2018, 13 Page Document.

*Primary Examiner* — Nadia A Mahmood

(57) ABSTRACT

An apparatus and method provides improved guidance instructions to providers of cardiopulmonary resuscitation (CPR) compressions in a cardiac arrest event. The apparatus detects CPR rate and/or changes in CPR rate, and issues prompts related to checking the depth of compressions based upon the rate/rate change detection. The prompts may be aural or visual.

15 Claims, 4 Drawing Sheets

(56) References Cited

U.S. PATENT DOCUMENTS

2014/0323928 A1  10/2014  Johnson
2015/0087919 A1   3/2015  Johnson et al.

FOREIGN PATENT DOCUMENTS

| WO | 2011100534 A1 | 8/2011 |
| WO | 2012075044 A2 | 6/2012 |

* cited by examiner

SMART PROMPTING TO IMPROVE RESPONDERS CPR PERFORMANCE

CROSS-REFERENCE TO PRIOR APPLICATIONS

This application is the U.S. National Phase application under 35 U.S.C. § 371 of International Application No. PCT/EP2018/075118, filed on Sep. 18, 2018, which claims the benefit of U.S. Provisional Patent Application No. 62/560,229, filed on Sep. 19, 2017. These applications are hereby incorporated by reference herein.

This invention relates to an improved apparatus and method for guiding a rescuer in the application of cardiopulmonary resuscitation chest compressions.

It has been demonstrated that responders who perform CPR and compress too fast often do not achieve the appropriate depth required for efficacious CPR compressions. One reason for this deficiency may be because it is physically challenging to compress deep and fast at the same time.

Some defibrillators incorporate user guidance prompting for cardiac rescues that includes prompted periods for applying CPR compressions, e.g. CPR "pause" periods, interleaved with prompted periods for "hands-off" ECG analysis for determining whether a defibrillating shock is needed, e.g. analysis periods. One such defibrillator which provides for an uninterruptible CPR pause period is described in U.S. patent application Ser. No. 11/917,511 filed Nov. 16, 2005 and entitled "AED HAVING MANDATORY PAUSE FOR ADMINISTERING CPR", the disclosure of which is herein incorporated by reference.

The prior art has addressed this problem in several ways. US20080145827A1 entitled "Signal Processing Device for Providing Feedback on Chest Compression in CPR" describes a depth measuring device and a force measuring device, the outputs of which provide CPR guidance to the user. US20140323928A1 entitled "Compression Depth Monitor with Variable Release Velocity Feedback" describes the use of an accelerometer in a chest-applied device to monitor for CPR-related chest displacements. And EP1491175A1 entitled "Cardio-pulmonary resuscitation device with feedback from measurement of pulse and/or blood oxygenation" describes a pulse sensor measuring a pulse rate of a victim and a SpO2 sensor measuring blood oxygenation. Electronics process the outputs of the sensors and determine actions of a rescuer who performs cardiopulmonary resuscitation (CPR). A prompting device conveys the actions to the rescuer.

The inventors have identified several problems with the prior art teachings such as those described above. Devices which directly sense depth and force of CPR compressions are relatively expensive. Such devices also typically are configured as ancillary inputs to other rescue gear such as defibrillators and monitors, and so require cables or wireless data connections. Such equipment has not been widely adopted by cardiac rescue agencies.

Prior art devices which monitor CPR compressions all require additional equipment for use during CPR. The delay entailed in the application of these devices detrimentally effects therapy. The devices also increase the complexity of the rescue. For example, guidance prompts to the rescuer tend to be lengthy (e.g. a continuous synchronization clock) and distracting from other efforts. For example, several prior art devices incorporate metronomes to try to keep the rate correct. Metronomes are effective to some degree, but some users will tire and change rates even with the sound. Overall, studies have shown that such prompting is difficult for the user in adjusting to a proper compressions rate and depth, especially over the entire duration of a rescue.

Thus what is needed is an improved apparatus and method of guiding CPR therapy which avoids the problems presented by the prior art.

The inventors have discovered that an incorrect rate of CPR compressions, and in particular a large change in the rate of CPR compressions, often corresponds to an incorrect depth of compressions as well. The inventors further realize that a prompt for responders to adjust their depth of compressions in response to the sensed rate of compressions or change in rate of compressions can be effective to guide the responder s to the correct depth. This improvement is enabled without the need for additional acceleration, force, or displacement sensors to be deployed at the patient's body. This discovery is also counter-intuitive to the prior art, which simply teaches prompts of adjusting depth based on sensed depth of compressions, of adjusting rate based on sensed rate of compressions, and other such prompts which correlate directly to the characteristic which needs adjustment.

The inventors have in particular discovered that by monitoring changes in the rate of compressions during CPR, they can ascertain when an appropriate prompt for depth of compressions should be provided. Thus a simple prompt to "pay attention to depth" in the presence of a large change in rate may actually guide the errant CPR provider to correct both of her depth of compressions and her rate of compressions. This feature may be incorporated into devices such as defibrillators which can more easily detect rate of compressions via trans-thoracic impedance changes but cannot easily detect depth of compressions. A particular advantage of this discovery is that more accurate CPR guidance can be obtained without the need to purchase and apply additional sensors such as accelerometers, force sensors, SpO2 sensors and the like.

In accordance with the principles of the present invention, and in one preferred embodiment of the invention, an automated external defibrillator (AED) for guiding the application of cardiopulmonary resuscitation (CPR) compressions is described. The AED comprises a pair of electrodes configured to obtain electrical signals related to changes in a transthoracic impedance related to a plurality of CPR compressions, a front end circuit in electrical communication with the pair of electrodes and configured to convert the electrical signals into a plurality of CPR compressions signals, a processor in communication with the front end circuit and configured to determine a CPR rate and a change in the CPR rate based upon the plurality of CPR compressions signals, and a user output configured to issue at least an aural CPR guidance prompt. The CPR guidance prompt is related to adjusting the depth of compression based upon a determined change in the CPR rate. Examples of the guidance prompt are "push hard", "push two inches", "check depth", and similar instructions related to depth. Another related guidance prompt may be "push harder."

In an alternative embodiment, the AED further issues at least an aural CPR guidance prompt related to adjusting the depth of compression based upon an inadequate CPR rate, such as a determined zero CPR rate, which persists for a predetermined duration of time.

In another preferred embodiment of the invention, a method for improving CPR guidance comprises a step of providing a device for guiding the application of cardiopulmonary resuscitation (CPR) compressions, the device including a housing, a sensor operable to detect a parameter related to a CPR compression and to output the parameter, a processor disposed in the housing, the processor configured to receive the parameter from the sensor, determine a CPR rate based on the parameter and determine a change in CPR rate from the CPR rate, and a user output configured to issue a CPR guidance prompt related to adjusting the depth of compression based upon the determined change in CPR rate. The method further comprises the steps of automatically detecting a change in the CPR rate by the device, and of issuing a guidance instruction related to a depth of compression based on the automatically detecting step. Examples of the guidance instruction are provided previously.

The method described above includes a number of alternative embodiments. The issuing step may issue at least an aural CPR guidance prompt related to adjusting the depth of compression based upon a determined zero CPR rate for a predetermined duration of time. The issuing step may occur only during a CPR pause period.

The inventive solution of identifying insufficient depth of compressions from CPR rate information enables more effective guidance of CPR while avoiding the cost, complexity, and confusion of deploying CPR displacement sensors at the rescue scene.

IN THE DRAWINGS

DETAILED DESCRIPTION OF THE EMBODIMENTS

Figure 1:
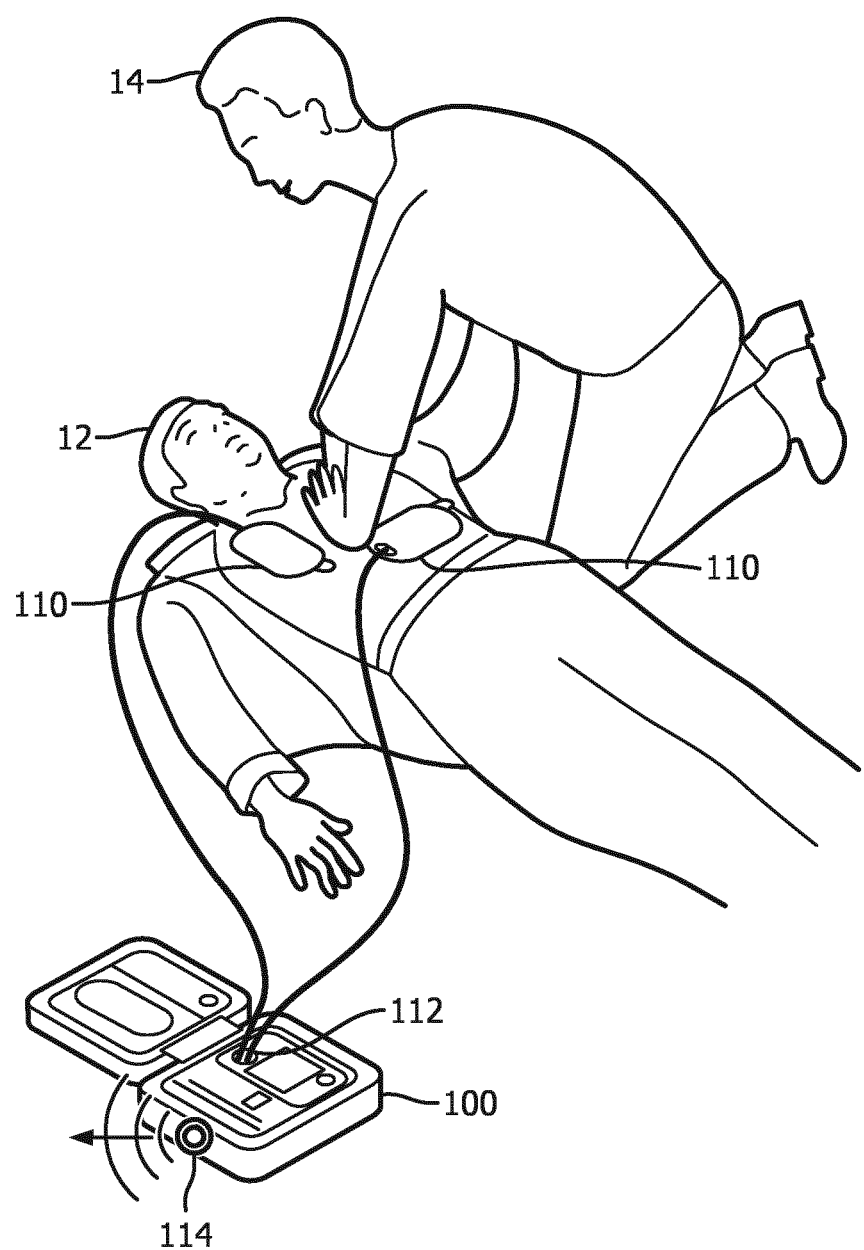
FIG. 1 illustrates an AED apparatus in use during a cardiac rescue.

As used herein for purposes of the present disclosure, the term "processor" is used generally to describe various apparatus relating to the operation of a medical apparatus, system, or method. A processor can be implemented in numerous ways (e.g., such as with dedicated hardware) to perform various functions discussed herein. A processor is also one example of a controller which employs one or more microprocessors that may be programmed using software (e.g., microcode) to perform various functions discussed herein. A controller may be implemented with or without employing a processor, and also may be implemented as a combination of dedicated hardware to perform some functions and a processor (e.g., one or more programmed microprocessors and associated circuitry) to perform other functions. Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more computer storage media (generically referred to herein as "memory," e.g., volatile and non-volatile computer memory such as RAM, PROM, EPROM, and EEPROM, floppy disks, compact disks, optical disks, magnetic tape, etc.). In some implementations, the storage media may be encoded with one or more programs that, when executed on one or more processors and/or controllers, perform at least some of the functions discussed herein. Various storage media may be fixed within a processor or controller or may be transportable, such that the one or more programs stored thereon can be loaded into a processor or controller so as to implement various aspects of the present invention discussed herein. The terms "program" or "computer program" are used herein in a generic sense to refer to any type of computer code (e.g., software or microcode) that can be employed to program one or more processors or controllers.

In various implementations, the terms "low-power standby circuit", "clock", "system monitor", "comparator" apply to components that are generally known in the art, and may be embodied in conventional microprocessors, application specific integrated circuits (ASICs), and field-programmable gate arrays (FPGAs), or may be integrated into the above described processor or controller. "Outputs" and "signals" may be understood to be electrical or optical energy impulses which represent a particular detection or processing result.

Automated external defibrillators ("AEDs") deliver a high-voltage impulse to the heart in order to restore normal rhythm and contractile function in patients who are experiencing arrhythmia, such as ventricular fibrillation ("VF") or ventricular tachycardia ("VT") that is not accompanied by a palpable pulse. There are several classes of defibrillators, including manual defibrillators, implantable defibrillators, and automatic external defibrillators. AEDs differ from manual defibrillators in that AEDs are pre-programmed to automatically analyze the electrocardiogram ("ECG") rhythm to determine if defibrillation is necessary and to provide administration measures such as shock sequences and CPR periods. There is no need, and in most cases no ability, for a rescuer to be concerned with setup of the rescue protocol. This differs from manual defibrillators which are used by expert medical professionals skilled at setting up all of the defibrillation parameters needed for a particular rescue.

FIG. 1 illustrates an AED 100 in use by a user 14 to resuscitate a patient 12 suffering from cardiac arrest. In sudden cardiac arrest, the patient is stricken with a life threatening interruption to the normal heart rhythm, typically in the form of VF or VT that is not accompanied by a palpable pulse (i.e., shockable VT). In VF, the normal rhythmic ventricular contractions are replaced by rapid, irregular twitching that results in ineffective and severely reduced pumping by the heart. If normal rhythm is not restored within a time frame commonly understood to be approximately 8 to 10 minutes, the patient will die. Conversely, the quicker defibrillation can be applied after the onset of VF, the better the chances that the patient 12 will survive the cardiac event.

To use the AED, a pair of electrodes 110 is applied across the chest of the patient 12 by the user 14 in order to acquire an ECG signal from the patient's heart. Electrodes 110 provide the ECG signals to the AED 100 internal circuitry via an electrical interface or electrode connector 112. The AED 100 then analyzes the ECG signal for signs of arrhythmia. If a treatable arrhythmia is detected, AED 100 arms itself and informs the user 14 via audible and visual prompts that a shock is advised. Typically, an audio speaker 114 emits aural prompts, such as "stay clear of the patient", "shock advised" and "press flashing shock button now" to guide the user. User 14 then presses the AED shock button to deliver a resuscitating defibrillation pulse via the electrodes 110 to the patient 12.

Effective SCA treatment typically involves both defibrillation and the application of CPR. FIG. 1 shows user 14 applying CPR compressions to the patient 12 chest. Most AEDs include a protocol which interleaves periods of ECG analysis and defibrillation, known as hands-off periods, with uninterruptible periods of CPR compressions, known as CPR pause periods. During the hands-off period, AED 100 warns the user 14 to remain clear of the patient 12 so that the ECG signals obtained by the pair of electrodes 110 is uncorrupted by signal artifact.

FIG. 1 shows that user 14 is applying CPR compressions during the CPR pause period. The electrical signals obtained across the sensor pair of ECG electrodes during the pause period are highly corrupted by electrical noise. Part of the noise stems from signal artifact generated by the motion of the patient 12 chest during CPR compressions. It has been shown that it is possible to obtain parameters related to the CPR compression rate from the electrical signals. A processor internal to the AED 100 can be configured to receive the CPR-related parameter and to determine both of a CPR rate and a trend or change in CPR rate from the parameter. But it also has proven impossible to accurately obtain CPR compressions depth information from the same signal. Thus, an AED 100 can generate guidance as to controlling a CPR rate from the ECG parameters, but not as to CPR depth.

Figure 2:
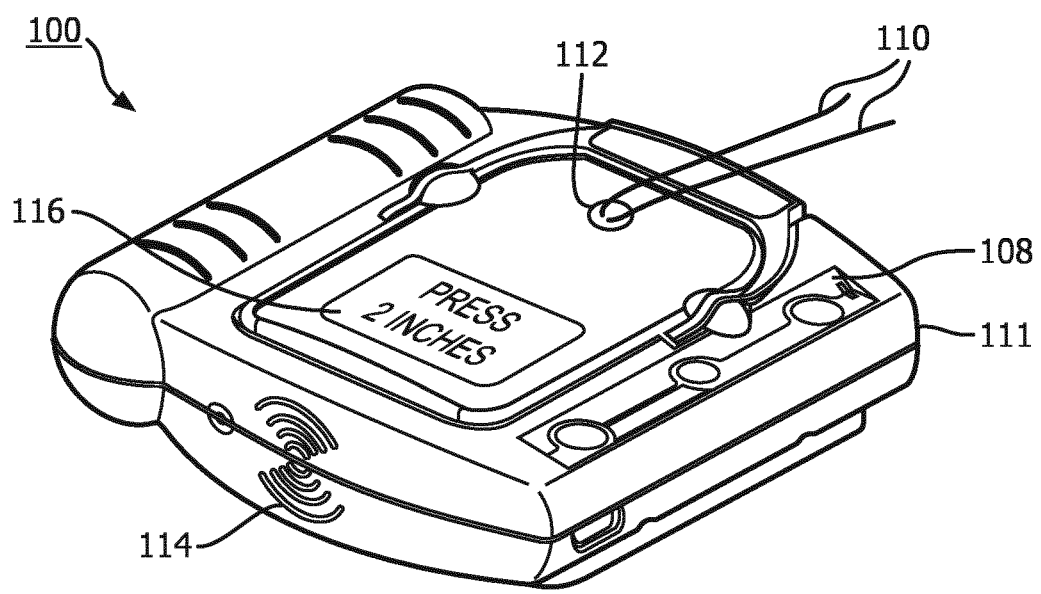
FIG. 2 illustrates an AED according to one embodiment of the invention.

FIG. 2 illustrates one embodiment of the inventive AED 100 as improved by the inventors. AED 100 is shown with several options for user outputs, including an audio speaker 114 for providing CPR-related voice prompts, a visual display 116 for providing CPR-related messages such as "Press 2 inches", and a blinking indicator light 108 such as an LED. The user outputs are arrayed optimally on the AED 100 housing 111, which also has electrode connector 112 to which the pair of electrodes 110 is connected. Housing 111 also contains internal signal processing, control, high voltage defibrillation circuits, computer memory, and power sources within a housing 111.

Figure 3:
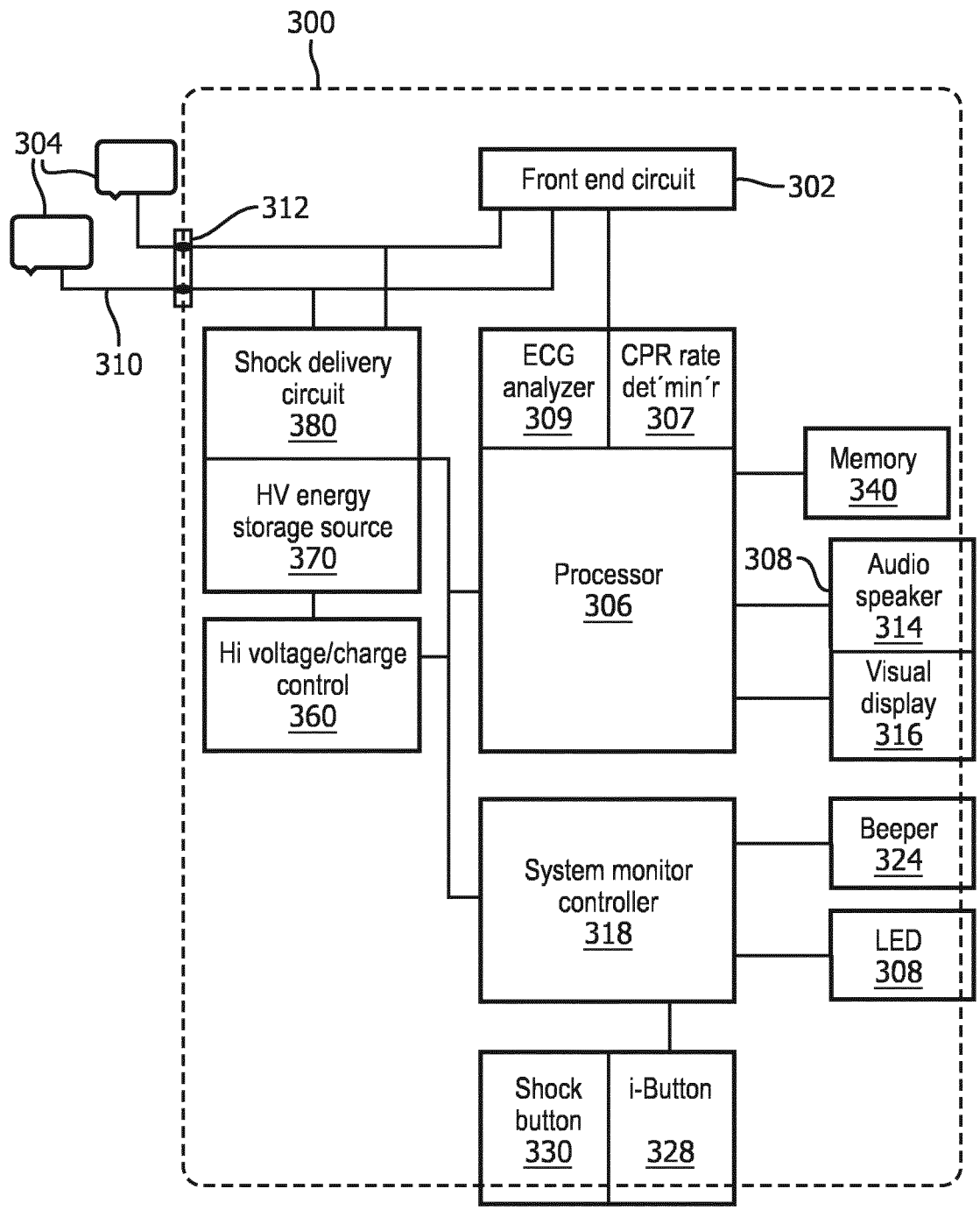
FIG. 3 illustrates an exemplary functional block diagram of the inventive apparatus.

FIG. 3 shows a functional block diagram of AED 100 which is configured for an improved guiding of the application of CPR compressions. In this embodiment, an AED 300 includes a pair of external electrodes 304 which are configured to be applied to a patient's skin. The electrodes 304 are also configured to obtain electrical signals related to changes in transthoracic impedance of the patient, and in particular to obtain electrical signals that are related to a plurality of CPR compressions as applied to the patient. The electrical signals may be direct transthoracic impedance (TTI) measurements or may be in the form of common mode current signals and the like.

The electrical signals are provided to the AED 300 circuitry via electrode leads 310 and electrode connector 312. AED 300 circuitry includes a front end circuit 302 which is configured to convert the obtained electrical signals into signals indicative of CPR compressions. Front end circuit 302 may include processing algorithms executed by hardware and software to obtain CPR compressions signals using methods as are known in the art. Such methods may adopt Fourier analysis or wavelet transforms and the like to determine a plurality of CPR compression signals from the electrical signal stream.

The plurality of CPR compressions signals is output from the front end circuit 302 and to a hardware processor 306. Hardware processor 306 is preferably a microprocessor executing instructions under control of a computer program and data that is stored in memory 340. Processor 306 is configured to determine a CPR rate and a trend of change in CPR rate over time from the compressions signals.

FIG. 3 optionally indicates that processor 306 may include sub-processor circuits for operating during different phases of the cardiac rescue protocol. For example, a dedicated CPR rate determination circuit 307 may be configured to improve the functionality of processor 306 by determining rate very quickly. In addition, processor 306 may hand some basic functions to a system monitor controller 318, which may itself be configured to provide low-power standby conditions functionality, or low-level control of a beeper 324, flashing LED status light 308, or the sensing of actuation on a shock button 330 and an informational request button 328.

Processor 306 compares one or both of the CPR rate and change in CPR rate over time to pre-determined ranges or thresholds which have values that are known to separate efficacious CPR from ineffective CPR. For example, a known efficacious range of CPR rate is from about 80 to about 130 compressions per minute. Guidelines prefer a constant rate of 100 compressions per minute. Acceptable variation to this rate is about +/−10 compressions per minute, or with very strict protocols at +/−5 compressions per minute. Similarly, a predetermined magnitude change in the CPR rate which may indicate the degradation of CPR from efficacious to ineffective may be about 40 compressions per minute, e.g. a responder slowing compressions from 120 to 80 compressions per minute or a responder increasing compressions from 90 to 130 compressions per minute. The former example may indicate that the responder is growing tired and is therefore not pushing hard enough. The latter example may indicate that the responder is pressing too shallowly in an attempt to speedup under fatigue. Processor 306 may optionally be configured to provide the CPR-related processing only during the non-interruptible CPR period. Of course, all of these CPR rates and changes in CPR rates for use in determining effective CPR can vary within the scope of the invention, but should be selected within a deviation that demonstrates the onset of ineffective CPR compressions.

Processor 306 is further configured to provide control of one or more user outputs, such as an audio speaker 314 or a visual display 316. The user outputs may be configured to issue a CPR guidance prompt based upon the rate or change of rate determinations described previously. A preferred embodiment of the user output is configured to issue an aural CPR guidance prompt from speaker 314 that is related to adjusting a depth of CPR compression based upon a determined change in the CPR rate.

The guidance prompt that is related to adjusting a depth of CPR compression may be of several forms and their equivalents. For example, the guidance prompt may comprise a visual or aural message to "push hard" or "push harder". The guidance prompt may comprise "push two inches", or "check depth". Any or all of these guidance prompts are directed to the user so that she may pay particular attention to potential improper depth of compressions that may occur when large changes in CPR rate occur. Visual guidance prompts may take the form of a graphic, a text message, or a dedicated LED/LCD light for example. Aural and visual prompts may occur simultaneously or complementarily, along with other appropriate indicators such as flashing lights from LED 308 or beeps from beeper 324 to attract the user attention.

Processor 306 may also generate CPR compressions depth-related guidance prompts based upon a detected CPR rate that is outside of a pre-determined CPR rate range which is known to be effective. The detected rate being ineffectively too slow or too fast causes the processor 306 and user output 314/316 to issue a prompt to "check depth" or "push two inches" for example. An effective range of CPR rates is from about 80-130 compressions per minute. If the CPR rate is detected at greater than about 130 compressions per minute, an aural prompt related to depth adjustment may be issued. Similarly, if a zero CPR rate is detected that lasts for a predetermined duration of time, for example for ten seconds during a CPR pause period, processor 306 and user output 314/316 may issue a prompt to "check depth." Ten seconds pause has been shown to be the threshold for the collapse of CPR-related perfusion pressure and is theorized to be harmful to the patient during CPR. The prompts thus bring to the user's attention an ineffective application of CPR compressions. Of course, the prompts to pay attention to depth may be accompanied by prompts to pay attention to rate as well.

If processor 306 is executing the ECG analysis period portion of the cardiac rescue protocol, then a dedicated ECG analyzer circuit 309 may be configured to improve processor 306 functionality by determining a shock/no-shock ECG condition very quickly. If a shock condition is detected, processor 306 provides a signal to a high voltage charger control circuit 360, which in turn charges a high voltage energy storage source 370, such as a capacitor, to a defibrillating voltage. Once this "armed" state is attained, and a shock condition persists, processor 306 issues an aural prompt to "press the shock button now" at speaker 314. A sensed press of the device shock button 330 causes processor 306 to deliver defibrillating current to the electrodes 304 via a shock delivery circuit 380.

Figure 4:
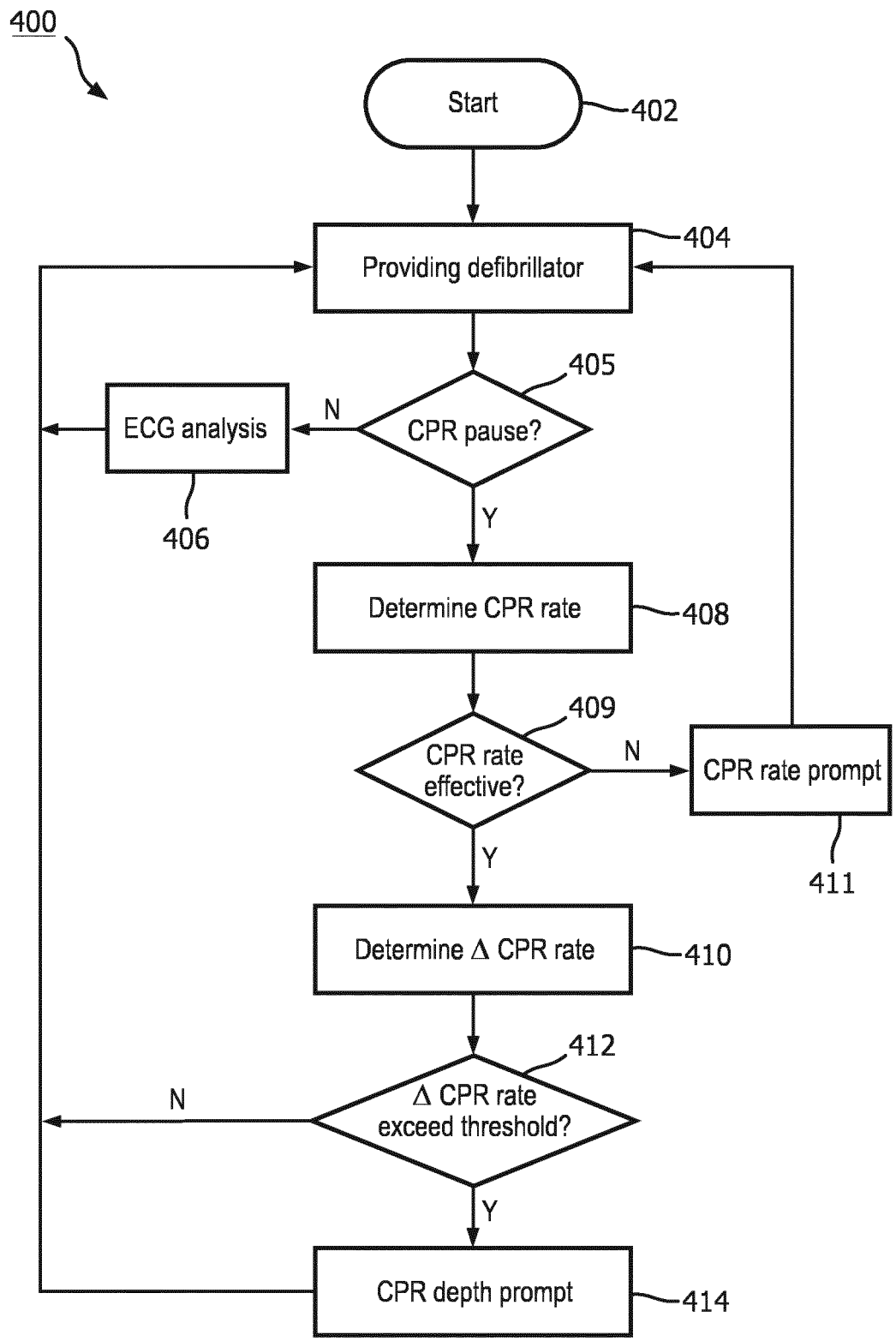
FIG. 4 illustrates a method flow chart of one exemplary inventive method for guiding the application of CPR compressions.

FIG. 4 illustrates a method 400 for improving CPR guidance from a device such as the afore-described AED, that is configured to guide the application of CPR. The method 400 is shown to begin with a start step 402 followed by a providing of the device step 404. The device provided in step 404 may be the AED described with respect to FIGS. 2 and 3 previously or another similar defibrillator. Alternatively, the providing step may be for a device that is dedicated to CPR monitoring or cardiac monitoring without including defibrillating components. The device is external to the patient and so includes housing, electrical circuits including a processor disposed in the housing and a user output configured to issue CPR guidance prompts related to adjusting the depth of compression based upon a determined change in CPR rate. A sensor is further provided that is in communication with the processor, the sensor configured to detect and output a parameter related to a CPR compression. A preferred sensor is the pair of electrodes 304 described previously, but can alternatively be in other forms. Blood pressure sensors, oxygenation sensors, breath sensors detecting pressure or flow from the patient's lungs, optical imagers of the patient or user during the rescue are examples of other sensors. Each sensor embodiment has the common characteristic of being configured to detect a CPR compression-related parameter.

The device provided in step 404 is deployed and activated to begin detecting the rate of CPR compressions at a determining CPR rate step 408. Examples of the particular CPR rate determining method and means is described previously. The output of determining step 408 is an instantaneous CPR compressions rate, such as 100 compressions per minute. Each CPR compressions rate data point is preferably stored in memory such that a time series of rates is obtained.

An automatically detecting step 410 detects a change in the CPR rate based upon the step 408 output from the device. The change in CPR rate is preferably calculated as a magnitude, but may also be identified as to direction (slowing or increasing rate over time). The time period over which the rate change is calculated may be of varying durations, but should preferably be less than the duration of one protocol period of CPR. Typical protocol periods of CPR are one minute, two minutes, or continuous. Therefore a desirable time period may be about thirty seconds or less.

Method 400 uses the determined change of CPR rate to control an issuing of a guidance instruction related to a depth of compression. One preferred control method is to compare the change in CPR rate to a predetermined threshold magnitude at a comparing step 412. Step 412 compares the determined change in CPR rate to a threshold such as the previously indicated 40 compressions per minute change. The threshold may be as small as about 5 compressions per minute change and as high as 50 compressions per minute change. If the method step 412 takes direction into account, the thresholds may differ. For example, if CPR rate slows down, a lesser magnitude threshold may prompt guidance than if the CPR rate has sped up. Other embodiments may dictate a greater magnitude threshold for guidance if the CPR rate slows down. Thresholds may also vary depending on the initial CPR rate. If, for example, the rate is at the slow end of effective rate, and the CPR rate slows down, a lesser magnitude threshold may apply that in the situation where the rate begins at the high end of the effective rate and the CPR rate slows down. If the determined change does not exceed the threshold at comparing step 412, then the method 400 returns to the providing step and repeats the CPR rate analysis steps. The repeating continues until the device is deactivated.

If the detected change in CPR rate at step 410 indicates that a degradation of CPR quality may have occurred, issuing step 414 issues a guidance instruction that is related to directing attention to the depth of ongoing CPR compressions. As shown in FIG. 4, issuing step 414 may be initiated in response to the change in CPR rate exceeding the predetermined threshold magnitude at step 412. As previously described, the nature of the CPR depth-related prompt may be to "push deeper", "push hard(er)", "push two inches", "check depth", and the like. The prompt may be output by one or more of an aural prompt from a speaker or by a visual guidance instruction text or graphic on a display, or by illuminated panel lights, etc.

Method 400 may optionally include a comparing step 409 for comparing the determined CPR rate from step 408 to a predetermined range of CPR rates which are known to be effective. If the determined CPR rate is within an effective range, previously exemplified as from about 80 compressions per minute to about 130 compressions per minute, the method proceeds to step 410. But if the determined CPR rate is outside of the known effective range, method 400 initiates a CPR rate guidance issuing step 411 to guide the user into the proper range. Step 411 may comprise the issuing of a depth-related prompt or more preferably of a rate-related prompt. The rate-related prompt may be such as "press faster", "slow down", "start pressing" and the like. After the guidance of step 411 is output from the user output, the method returns to the providing step 404 and repeats. By conducting this step of checking CPR rate prior to checking the change in CPR rate, the device can first guide the user into the proper application of CPR, and can then subsequently assess whether the user may be departing from the proper application of CPR. This arrangement of steps avoids the issuing of unnecessary and confusing guidance at the very beginning of the rescue when the rescuer is just coming up to the proper rate of CPR compressions.

Another optional embodiment of method 400 includes the providing step 404 processor being configured to execute a cardiac rescue protocol that includes a non-interruptible CPR pause period during which the user output is configured to automatically issue guidance prompts related to providing CPR compressions and an ECG analysis period during which the user output is configured to automatically issue guidance prompts related to refraining from CPR compressions. Before conducting the CPR-related analysis steps 408 through 414, method 400 first determines at step 405 which of the ECG analysis period and the non-interruptible CPR pause period the protocol is in. If in the ECG analysis period, no CPR related analysis should be conducted, and method 400 proceeds to ECG analysis conducting step 406. Thereafter, the method returns to the providing step 404 and repeats.

Only if the protocol is determined at step 405 to be in the non-interruptible CPR pause period does method 400 proceed to the CPR guidance steps starting at determining step 408. This discrimination between use during the two periods minimizes the possibility of the processor 406 confusing CPR-related compressions signals with ECG-related signals, and thus minimizes the possibility of erroneous guidance instructions of shock/no-shock decisions.

Modifications to the device, method, and displays as described above are encompassed within the scope of the invention. For example, similar and obvious modifications of the described aural and visual prompts fall within the scope of the invention.

What is claimed is:

1. An automated external defibrillator for guiding the application of cardiopulmonary resuscitation (CPR) compressions, comprising:
    a pair of electrodes configured to obtain electrical signals related to changes in a transthoracic impedance related to a plurality of CPR compressions;
    a front end circuit in electrical communication with the pair of electrodes and configured to convert the electrical signals into a plurality of CPR compressions signals;
    a hardware processor in communication with the front end circuit and configured to determine a CPR rate and a change in the CPR rate based upon the plurality of CPR compressions signals; and
    a user output configured to issue at least an aural CPR guidance prompt related to adjusting the depth of compression based upon a determined change in the CPR rate.

2. The automated external defibrillator of claim 1, wherein the electrical signals are selected from one of transthoracic impedance signals or common mode current signals.

3. The automated external defibrillator of claim 1, wherein the user output comprises one or more of an audio speaker and a visual display, and further wherein the CPR guidance prompt comprises a "push hard" prompt.

4. The automated external defibrillator of claim 1, further comprising one or more of an audio speaker and a visual display, and further wherein the CPR guidance prompt comprises a "push two inches" prompt.

5. The automated external defibrillator of claim 1, wherein the user output is further configured to issue at least an aural CPR guidance prompt related to adjusting the depth of compression based upon a determined zero CPR rate for a predetermined duration of time.

6. The automated external defibrillator of claim 5, wherein the predetermined duration of time is less than about 10 seconds.

7. The automated external defibrillator of claim 1, wherein the user output is further configured to issue at least an aural CPR guidance prompt related to adjusting the depth of compression based upon a determined CPR rate that is known to be ineffective.

8. The automated external defibrillator of claim 7, wherein the determined CPR rate is greater than about 130 compressions per minute.

9. The automated external defibrillator of claim 1, wherein the determined change in the CPR rate is a magnitude of about 40 compressions per minute.

10. A method for improving CPR guidance, comprising the steps of:
    providing a device for guiding the application of cardiopulmonary resuscitation (CPR) compressions, the device including a housing, a sensor operable to detect a parameter related to a CPR compression and to output the parameter, a processor disposed in the housing, the processor configured to receive the parameter from the sensor, determine a CPR rate based on the parameter and determine a change in CPR rate from the CPR rate, and a user output configured to issue a CPR guidance prompt related to adjusting the depth of compression based upon the determined change in CPR rate;
    automatically detecting the change in the CPR rate by the device; and
    issuing a guidance instruction related to a depth of compression based on the automatically detecting step.

11. The method of claim 10, further comprising the steps of:
    comparing the change in CPR rate to a predetermined high threshold of a change in CPR rate, and
    issuing the guidance instruction if the detected change in the CPR rate exceeds the threshold.

12. The method of claim 11, wherein the high threshold of a change in CPR rate is about 40 compressions per minute.

13. The method of claim 10, further comprising a step, prior to the automatically detecting step, of determining a CPR rate that is within a range that is known to be effective.

14. The method of claim 10, wherein the processor in the providing step is further configured to execute a cardiac rescue protocol that includes a non-interruptible CPR pause period during which the user output is configured to automatically issue guidance prompts related to providing CPR compressions and an ECG analysis period during which the user output is configured to automatically issue guidance prompts related to refraining from CPR compressions, wherein the automatically detecting step occurs only during the non-interruptible CPR pause period.

15. The method of claim 10, wherein the issuing step comprises one of an audible and visual guidance instruction to "push hard".

* * * * *